US007666660B2

(12) United States Patent
Krylov et al.

(10) Patent No.: US 7,666,660 B2
(45) Date of Patent: Feb. 23, 2010

(54) METHOD FOR MIXING INSIDE A CAPILLARY AND DEVICES FOR ACHIEVING SAME

(76) Inventors: Sergey N. Krylov, 45 Quaker Ridge Rd., Concord, Ontario (CA) L4K 2E5; Victor Okhonin, 6 Assiniboine, apt. #205, North York, Ontario (CA) M3J 1L3

( * ) Notice: Subject to any disclaimer, the term of this patent is extended or adjusted under 35 U.S.C. 154(b) by 0 days.

(21) Appl. No.: 11/412,927

(22) Filed: Apr. 28, 2006

(65) Prior Publication Data
US 2006/0289059 A1 Dec. 28, 2006

Related U.S. Application Data

(60) Provisional application No. 60/675,458, filed on Apr. 28, 2005.

(30) Foreign Application Priority Data

Apr. 28, 2005 (CA) .................................. 2505657

(51) Int. Cl.
*C12M 1/36* (2006.01)
(52) U.S. Cl. ........................... 435/286.7; 137/2; 137/3; 137/7; 137/12
(58) Field of Classification Search ........................ None
See application file for complete search history.

(56) References Cited

U.S. PATENT DOCUMENTS

2001/0055817 A1* 12/2001 Malmqvist et al. .......... 436/531
2003/0040105 A1* 2/2003 Sklar et al. ............... 435/287.2
2005/0032202 A1* 2/2005 Laurell et al. ............ 435/287.2

OTHER PUBLICATIONS

Korenaga et al., Dispersion behavior of solutes in an ideal laminar flow with small-bore glass tubes, 1989, Bull Chem Soc Jpn 62(5): pp. 1492-1500.*
Arkhipov et al., Cytometry Part A, 63A:41-47, 2005 (e-pub 2004).
Berezovski et al., Electrophoresis, 23:3398-3403, 2002.
Culbertson and Jorgenson, Anal. Chem., 66(7):955-962, 1994.
Daviss, B., The Scientist, 19(4):27-29, 2005.
Gas et al., J. Chromatogr. A, 709:63-68, 1995.
Griffiths and Nilson, Anal. Chem., 71:5522-5529, 1999.
Hellmich et al., Electrophoresis, 26:3689-3696, 2005.
Hunter and Carta, J. Chromatogr. A, 971:105-116, 2002.
Kinzer et al., Anal. Chem., 68(18):3250-3257, 1996.
Krylov et al., Cytometry, 37:14-20, 1999.
Lee et al., J. Chromatogr. A, 1053:173-179, 2004.
McGuffin, V.L., Electrophoresis, 22:3709-3719, 2001.
Moser et al., Anal. Chim. Acta, 558:102-109, 2006.
Rondelez et al., Nat. Biotech., 23(3):361-365, 2005.
Sharma et al., Anal. Chem., 77(3):806-813, 2005.
Steger et al., JALA, 9:291-299, 2004.
Taga and Honda, J. Chromatogr. A, 742:243-250, 1996.

* cited by examiner

*Primary Examiner*—N. C. Yang
(74) *Attorney, Agent, or Firm*—Bereskin & Parr LLP/S.E.N.C.R.L., s.r.l.; Patricia Folkins

(57) ABSTRACT

The present invention provides a method for mixing three or more fluids inside a capillary. The present invention further provides a method for optimizing efficient mixing of two or more fluids inside a capillary, and a computer-readable medium for use by a processor to carry out this method. Additionally, the present invention provides an automated system for mixing two or more fluids inside a capillary. Also provided is a system for optimizing efficient mixing of two or more fluids inside a capillary.

26 Claims, 9 Drawing Sheets

METHOD FOR MIXING INSIDE A CAPILLARY AND DEVICES FOR ACHIEVING SAME

RELATED APPLICATIONS

This application claims the benefit of U.S. Provisional Application No. 60/675,458, filed Apr. 28, 2005, the contents of which are incorporated herein by reference. This application also claims the benefit of Canadian Application No. 2,505,657, filed Apr. 28, 2005, the contents of which are incorporated herein by reference.

BACKGROUND OF THE INVENTION

Many antibodies, ligand receptors, regulatory enzymes (e.g., kinases, glycosyltransferases, and lipid transferases), and other biomolecules are attractive therapeutic targets. Antigens, ligands, peptides, substrates, and small molecules that bind to, activate, and/or inhibit these biomolecules are considered to be potential drug candidates. High-throughput screening of combinatorial libraries of potential drug candidates is pivotal to the identification of large numbers of lead compounds for drug development.

Methods of screening for reagents that bind to, and modulate, biomolecules can be divided into two broad categories: homogeneous methods and separation-based methods. In homogeneous methods, the formation of a reaction product is monitored without its separation from any unreacted reagents. In separation-based methods, the reaction product is separated from any unreacted reagents by chromatography (e.g., capillary chromatography) or electrophoresis (e.g., capillary electrophoresis), prior to detection. An "ideal" method for high-throughput screening should require only nanoliter volumes of the biomolecule and the candidate drug.

Microreactors, which facilitate chemical processes in nanoliter and sub-nanoliter volumes, are highly attractive for high-throughput screening (Steger et al., The dispensing well plate: a novel device for nanoliter liquid handling in ultra high-throughput screening. *Journal of the Association for Laboratory Automation*, 9(5):291-99, 2004) and a variety of other applications, including multiplexed bioanalyses (Moser et al., Microsphere sedimentation arrays for multiplexed bioanalytics. *Analytica Chimica Acta*, 558:102-09, 2006), studies of single molecules (Lee et al., Single-molecule spectroscopy for molecular identification in capillary electrophoresis. *J. Chromatogr., A.*, 1053:173-79, 2004), and analyses of the chemical contents of single cells (Hellmich et al., Single cell manipulation, analytics, and label-free protein detection in microfluidic devices for systems nanobiology. *Electrophoresis*, 26:3689-696, 2005). The primary requirements for microreactors include: (i) easy and reproducible mixing, (ii) negligible evaporation, and (iii) interfacing with sensitive and informative analytical tools. These requirements can be met, for example, by confining the nanoliter-volume reaction mixture in a microfabricated well (Chang et al., A microfabricated device for the characterization of biological species. *Journal of Vacuum Science and Technology B*, 20(5): 2058-064, 2002), oil drop (Hiroyauki, Noji, Single cell manipulation, analytics, and label-free protein detection in microfluidic devices for systems nanobiology, *Nature Biotech.*, 23:361-65, 2005), or capillary format (Shen et al., Capillary sodium dodecyl sulfate-DALT electrophoresis of proteins in a single human cancer cell, *Electrophoresis*, 22(17):3677-682).

The known formats for microreactors have their specific advantages and limitations. For example, the well and oil-drop formats require precise microprinting instrumentation for accurate mixing of reactants. Additionally, the well format may require complicated technological solutions for closing the wells to prevent evaporation. Both of these formats are not easily interfaced with separation techniques and are limited to in situ optical detection. Furthermore, these two formats require either the use of relatively noisy fluorophore-quencher systems for monitoring non-covalent binding or the use of rare fluorogenic substrates for studying enzymatic reactions.

Capillaries perfectly suit the evaporation and analysis requirements of microreactors. Indeed, due to the extremely small liquid-air interface at the capillary orifice, evaporation can be neglected for as long as days. In addition, capillary microreactors are naturally interfaced with highly-efficient analytical techniques, such as capillary electrophoresis and chromatography. In turn, capillary separation can be readily interfaced with different types of detection, including optical, electrochemical, and mass spectrometric detection, thereby providing ultimate analytical capabilities. However, to date, the challenge that has prevented the widespread practical application of capillary microreactors has been the requirement for easy and reproducible mixing of reactants.

Two methods have been proposed for mixing reactants inside capillaries: electrokinetic mixing and mixing by longitudinal diffusion. However, as discussed below, neither of these methods provides a generic way of mixing reactants in a capillary, which is required for practical application of capillary microreactors.

Electrokinetic mixing is based on different velocities of reactants in an electric field applied to the ends of a capillary (Hiroyauki, N., *Nature Biotech.*, 23:361-65, 2005). This mode of mixing requires knowledge of the electrophoretic mobilities of the reactants; this cannot be calculated, and should be experimentally determined. Electrokinetic mixing becomes impractical when the reactants are dissolved in different buffers, or when three or more reactants are to be mixed.

Mixing by longitudinal diffusion is based on diffusion through transverse interfaces between separately-injected plugs of reactants (Okhonin et al., Transverse diffusion of laminar flow profiles to produce capillary nanoreactors. *Anal. Chem.*, 77:5925-929, 2005). The characteristic length of an injected plug is 1 mm; several plugs have a cumulative length of several millimetres. Longitudinal diffusion through several millimetres can take as long as several hours. Thus, longitudinal diffusion is impractical for a typical geometry of plugs. Furthermore, it is inapplicable to the mixing of three or more reagents inside a capillary (see, e.g., Taga and Honda, *J. Chromatogr., A.*, 742:243-50, 1996).

Due to the lack of a generic approach to mixing multiple reagents inside a capillary, capillary separation has, until now, required pre-mixing components in a vial outside of the capillary. This limits the minimum volume of reagents consumed per analysis to approximately 1 µL—three orders of magnitude greater than the requirement. This results in wastage of the reagents. Additionally, if mixing by longitudinal diffusion is performed for studies of reactions, the reactions can proceed to a significant extent because longitudinal diffusion takes a very long time; this will prevent separate modeling of mixing and reaction kinetics. Simultaneous modeling of mixing and reaction kinetics is much more demanding, as it requires the knowledge of rate constants, which are often not available.

Accordingly, in view of the foregoing, there exists in the art a need for a separation-based method of drug screening that requires only nanoliter or subnanoliter volumes of reagents and permits two or more reagents to be mixed inside a capillary. There also exists in the art a need for a universal numerical model which accurately simulates mixing of two or more reagents inside a capillary.

SUMMARY OF THE INVENTION

The inventors demonstrate herein the transverse diffusion of laminar-flow profiles (TDLFP): the first generic method for mixing multiple reagents inside a capillary. Solutions of reagents are injected inside the capillary, by pressure, as a series of consecutive plugs. Due to the laminar nature of flow inside the capillary, the non-diffused plugs have parabolic profiles with predominantly longitudinal interfaces between the plugs; thus, the ratio of plug length to capillary diameter is extremely large. After injection, the reagents are mixed by transverse diffusion; the contribution of longitudinal diffusion to mixing is negligible. In accordance with this method, nanoliter amounts of liquids can be mixed inside a capillary. The method is beneficial in overcoming problems, including wastage of reagents, associated with mixture outside of the capillary.

Being a generic method, TDLFP allows the mixing of multiple reagents, without knowledge of their physical-chemical properties. The combination of TDLFP and capillary separation provides an indispensable tool for use in screening large combinatorial libraries for affinity probes and drug candidates. A few microliters of a target protein, for example, will be sufficient to screen thousands of compounds.

The inventors further present herein a universal mathematical model of TDLFP which does not require simplifying assumptions. The model is based on a numerical algorithm for solving mass-transfer equations; it was used to study mixing of multiple (e.g., two, three, four, etc.) solutions inside a capillary. The inventors discovered that TDLFP can mix multiple solutions with the overlap efficiency of 89%, 80%, and 57%, respectively, as discussed below. In accordance with the inventors' model, parameters are optimized for efficient mixing, inside the capillary, of multiple (e.g., two, three, four, etc.) reactants that are separately injected. The inventors' model provides an important tool for studying TDLFP and for developing practical applications of TDLFP as a means of mixing reactants in capillary microreactors (e.g., in studies of three-reactant systems, such as enzyme-substrate-substrate systems and enzyme-substrate-inhibitor systems).

Accordingly, in one aspect, the present invention provides a method for mixing three or more fluids inside a capillary tube, by: (a) sequentially introducing the three or more fluids into the capillary tube by pressure injection, under conditions of laminar flow; and (b) allowing the fluids to mix inside the capillary tube by diffusion.

By way of example, each of the fluids may be a liquid or solution. For example, in one embodiment, at least one fluid is a solvent, and at least one solute is mixed with the solvent. In another embodiment, each of the fluids includes an antibody, an antigen, an aptamer, a buffer, DNA, an enzyme, an enzyme inhibitor, an enzyme substrate, a ligand, a ligand receptor, a protein, or RNA.

Each of the fluids may be introduced into the capillary tube as a plug of fluid having a non-rectangular concentration profile inside the capillary tube. In one embodiment, the non-rectangular concentration profile is a parabolic profile. In another embodiment, each of the fluids is introduced into the capillary tube with an introduction time of 1 second or less. In still another embodiment, the capillary tube is a channel in a microfabricated device.

In certain embodiments of the present invention, the fluids include at least two reagents, and a reaction occurs inside the capillary tube upon mixing. Therefore, the method may also include the step of separating reaction components, such as unused reagent and reaction product (e.g., by capillary electrophoresis or capillary chromatography). In one embodiment, the step of separating reaction components includes detecting the reaction components during or following separation (e.g., the reaction components are detected inside the capillary tube, or upon exiting the capillary tube, by absorbance, chemiluminescence, fluorescence, mass spectrometry, an electrochemical detector, etc.).

The at least two reagents may include at least one antigen and at least one antibody; at least one aptamer and at least one target thereof; at least one DNA-binding protein and at least one DNA; at least one RNA-binding protein and at least one RNA; at least one drug candidate and at least one therapeutic target (e.g., a protein); at least one enzyme and at least one enzyme substrate; or at least one ligand and at least one receptor. Therefore, the method may further include the step of detecting or measuring binding between the at least two reagents.

For example, in certain embodiments, the at least two reagents include at least one enzyme and at least one enzyme substrate. Therefore, the method may also include the step of screening for at least one enzyme-substrate complex or for at least one enzyme inhibitor (e.g., by measuring inhibition efficiency of the at least one enzyme inhibitor).

Additionally, in certain embodiments, the at least two reagents include at least one drug candidate and at least one therapeutic target (e.g., a protein). Therefore, the method may also include the step of detecting or measuring binding of the drug candidate and the therapeutic target (e.g., in high-throughput screening) and/or screening for at least one drug-target complex.

The method of the present invention may also include the step of optimizing (e.g., optimizing the efficiency of) step (a) and/or step (b) by analyzing laminar flow profiles of the three or more fluids inside the capillary tube. In one embodiment, the optimizing step includes at least one of: (a) calculating concentration profiles of the three or more fluids inside the capillary tube; and (b) calculating rates of a chemical reaction (e.g., an enzymatic reaction) inside the capillary tube. By way of example, laminar flow profiles may be analyzed using at least one parameter of mixing (e.g., a coefficient of diffusion of a molecule inside the capillary tube, a diameter of the capillary tube, a time of introduction of a fluid into the capillary tube, a time of incubation of a fluid inside the capillary tube, the number of fluids to be mixed inside the capillary tube, position of at least one fluid on an array of fluids to be mixed inside the capillary tube, molecular weight of at least one solute in at least one fluid to be mixed inside the capillary tube, viscosity of at least one fluid inside the capillary tube, viscosity of at least one fluid to be mixed inside the capillary tube, and volume of at least one fluid to be mixed inside the capillary tube).

In one embodiment, the optimizing step includes introducing a buffer (e.g., a blank buffer) into the capillary tube. In another embodiment, the optimizing step includes analyzing diffusion of the laminar flow profiles. The optimizing step may also include use of a computer program. In yet another embodiment, the optimizing step includes introducing each of the three or more fluids into the capillary tube with an introduction time of 1 second or less.

In another aspect, the present invention provides a method for optimizing efficient mixing of two or more fluids inside a capillary tube, by analyzing laminar flow profiles of the two or more fluids inside the capillary tube. Also provided is a computer-readable medium having recorded thereon statements and instructions for execution by a processor to carry out this method.

In yet another aspect, the present invention provides a method for optimizing efficient mixing of two or more fluids inside a capillary tube, the method implemented by a computer including at least one processor, the method including: (a) receiving input in response to a user prompt, the input including at least one parameter of mixing; and (b) using the input to analyze laminar flow profiles of the two or more fluids inside the capillary tube. Exemplary parameters of mixing include, without limitation, a coefficient of diffusion of a molecule inside the capillary tube, a diameter of the capillary tube, a time of introduction of a fluid into the capillary tube, a time of incubation of a fluid inside the capillary tube, the number of fluids to be mixed inside the capillary tube, position of at least one fluid on an array of fluids to be mixed inside the capillary tube, molecular weight of at least one solute in at least one fluid to be mixed inside the capillary tube, viscosity of at least one fluid inside the capillary tube, viscosity of at least one fluid to be mixed inside the capillary tube, and volume of at least one fluid to be mixed inside the capillary tube.

In one embodiment, the analyzing step uses an algorithm of mixing that includes at least one optimized parameter of mixing (e.g., the number of fluids to be mixed inside the capillary tube, the order in which fluids are introduced into the capillary tube, the presence or the absence of a buffer plug inside the capillary tube, a time of introduction of a fluid into the capillary tube, a time of incubation of a fluid inside the capillary tube, and a time of reaction of a chemical reaction inside the capillary tube). In another embodiment, the analyzing step includes calculating a concentration profile for at least one of the fluids inside the capillary tube. In still another embodiment, the analyzing step includes calculating at least one rate of a chemical reaction (e.g., an enzymatic reaction) inside the capillary tube. The chemical reaction may include formation of a complex (e.g., a complex that includes a protein and a candidate drug).

In still another aspect, the present invention provides an automated system for mixing two or more fluids inside a capillary tube, including: (a) a robot for inserting a capillary tube into at least one container housed within the system, the at least one container providing a source for at least one fluid to be introduced inside the capillary tube at a first end of the capillary tube; (b) pump means for applying a pressure change between the first end and a second end of the capillary tube, whereby a fluid in the at least one container may be introduced inside the capillary tube; (c) temperature control means for controlling temperature inside the capillary tube; and (d) a processor adapted to analyze laminar flow profiles of the two or more fluids inside the capillary tube, so as to optimize mixing of the two or more fluids inside the capillary tube. The automated system may also include at least one detecting device (e.g., a device for detecting absorbance, a device for capillary electrophoresis, a device for capillary chromatography, a device for detecting chemiluminescence, a device for detecting fluorescence, a device for electrochemical detection, and a device for mass spectrometry) coupled to the capillary tube at, or near, an end thereof. In one embodiment, each of the two or more fluids is introduced into the capillary tube with an introduction time of 1 second or less.

In a further aspect, the present invention provides a system for optimizing efficient mixing of two or more fluids inside a capillary tube, including at least one computing device including software that, when executed, performs a method that includes analyzing laminar flow profiles of the two or more fluids inside the capillary tube.

Additional aspects of the present invention will be apparent in view of the description which follows.

DETAILED DESCRIPTION OF THE INVENTION

Figure 1:
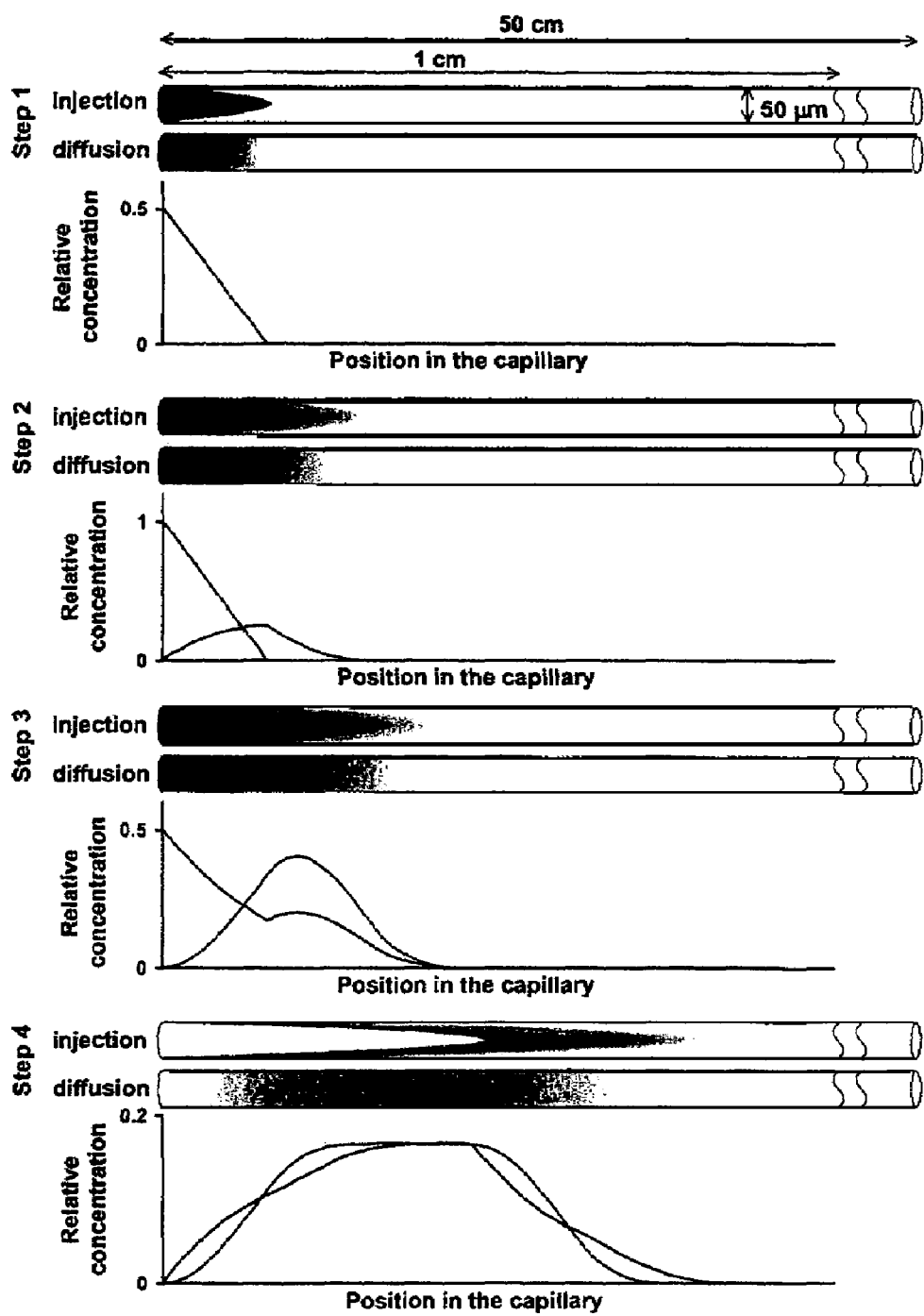
FIG. 1 depicts simulated mixing of two components, blue and red, inside a capillary by transverse diffusion of parabolic profiles. The white colour inside the capillary represents the blank buffer. The graphs show concentration profiles of the two components inside the capillary after every step. The coloured plugs have identical lengths; the white plug is 3 times longer than each of the coloured plugs.

A capillary, or capillary tube, is an attractive chemical nanoreactor for analytical applications. Reactions in the capillary can be carried out in nanoliter volumes. The products can be separated from the reagents inside the same capillary, using capillary chromatography or electrophoresis. In addition, the capillary can be easily interfaced with optical, electrochemical, and mass-spectrometric detectors, thereby offering ultimate analytical capabilities. However, prior to the present invention, the fundamental problem which has hampered the use of capillary nanoreactors has been the lack of a generic method for mixing reagents inside the capillary.

As discussed herein, the inventors have proved the concept of transverse diffusion of laminar-flow profiles (TDLFP), both theoretically and experimentally. In particular, the inventors have developed a simple mathematical model of TDLFP, and have used it to simulate mixing of two solutions. Furthermore, the inventors have confirmed the results of simulation experimentally, by mixing and reacting, inside the capillary, an enzyme and its substrate. The inventors have also extended TDLFP to mixing three reactants, thereby permitting capillary microreactors to be used for studies of multiple-reactant systems (e.g., enzyme-substrate-substrate systems and enzyme-substrate-inhibitor systems). To achieve accurate simulation of TDLFP mixing of three reagents, for example, the inventors designed a universal numerical model which does not require simplifying assumptions.

In accordance with TDLFP-based mixing, solutions of reagents may be injected inside a capillary, by pressure, as a series of consecutive plugs. The length of every plug is typically much greater than the diameter of the capillary. Due to the laminar nature of the flow inside the capillary, the non-diffused plugs have parabolic profiles with predominantly-longitudinal interfaces between the plugs. After the injection, the reagents are mixed by transverse diffusion; the contribution of longitudinal diffusion to mixing is negligible. Due to the narrow diameter of the capillary, mixing by transverse diffusion is fast. Moreover, the time of mixing is independent of the length of plugs; it solely depends on the diameter of the capillary and the diffusion coefficients of the substances mixed.

TDLFP-based mixing has a number of advantages over classical mixing in a vial. Classical mixing in a vial relies on the creation of vortexes—complex hydrodynamic structures—which are difficult to model. As a result, classical mixing is largely unpredictable. In contrast, TDLFP relies on the diffusion of laminar flows, which can be accurately modeled using simple mathematics. The simple non-numerical mathematical model of TDLFP (Example 2) relies on three simplifying assumptions that are easily achieved: (i) longitudinal diffusion was negligible during the entire procedure of mixing; (ii) transverse diffusion was negligible during injection of plugs; and (iii) transverse diffusion resulted in elimination of concentration gradients in the transverse direction between plug injections. The first assumption is achieved by high length-to-diameter ratios of the plugs; the second and third assumptions are achieved by prolonging the period of time between injections to the characteristic diffusion time for the largest reagent injected in the capillary. The three assumptions are essential only for simplifying the mathematical model. As described herein, the inventors also designed a universal numerical model, which does not require simplifying assumptions, in order to achieve accurate simulation of TDLFP mixing of three reactants.

Diffusion is a slow process; however, TDLFP-based mixing is possible due to the small diameter of the capillary. Mixing time can range from seconds to minutes, depending on the size of mixed molecules and the number of steps in mixing. When studying kinetics with TDLFP-based mixing, the concentrations of reagents should typically be chosen so that mixing kinetics are faster than reaction kinetics.

TDLFP represents the first generic method for efficient and controlled mixing of reagents inside the capillary. The method overcomes the long-standing limitation of capillary nanoreactors, and prepares the way for their wide practical use. TDLFP becomes especially attractive when it is combined with capillary separation tools. It is expected that the combination of TDLFP with capillary chromatography and electrophoresis will be indispensable in screening large combinatorial libraries for affinity probes and drug candidates—in part, because a few microliters of a target protein will be sufficient to screen thousands of compounds, with a screen of each compound consuming only nanoliters of fluid. It is also believed that capillary mixing could revolutionize chemical cytometry (Krylov et al., *Cytometry*, 37:14-20, 1999; Arkhipov et al., *Cytometry*, 63A:41-47, 2005; Davis, B., *The Scientist*, 19(4):27-29, 2005), by providing a universal tool for cell lysis and for labeling intracellular components (e.g., with affinity probes, hybridization probes, etc.).

Accordingly, the present invention provides a method for mixing three or more (e.g., 3, 4, 5, 6, 7, 8, etc.) fluids inside a capillary tube. As used herein, the terms "capillary tube" and "capillary" include any hollow tube, as well as any channel, conduit, passage, etc., that permits the flow of a liquid or gas, particularly under specified conditions (e.g., of temperature, pressure, etc.). The capillary cross-section may be of round, square, rectangular, or any other shape. Typically, a capillary has a channel (for non-round capillaries) or inner diameter (for round capillaries) that is characteristically small (e.g., less than 1 mm, and, frequently, no greater than 100 μm). The capillary tube of the present invention may have any length and diameter, but is typically of a size to permit handling of picoliter to microliter volumes of fluid. In one embodiment, the capillary inner diameter is of the order of 20-100 micrometers (μm), and the capillary length is of the order of 10-100 centimeters (cm). The capillary of the present invention has at least two ends, but may have more if bifurcated or branching. In one embodiment, the capillary tube is a preformed channel in a microfabricated device or chip (e.g., a "lab on a chip"). Preferably, the capillary of the present invention is adapted for use in capillary electrophoresis, capillary chromatography, and/or any other small-volume separation techniques.

Fluids for use in the method of the present invention may include, without limitation, liquids. In one embodiment, the fluids are all liquids. Suitable liquids include, without limitation, water and a solution (e.g., a homogeneous mixture of two or more substances). A solution of the present invention may comprise one or more solvents and one or more solutes. In one embodiment, the solution is a buffer—a fluid which is devoid of any solute. By way of example, a fluid of the present method may comprise an antibody, an antigen, an aptamer, a buffer, DNA, an enzyme, an enzyme inhibitor, an enzyme substrate, a ligand, a ligand receptor, a protein, RNA, and/or any other reagent or reactant. As used herein, a "reagent" or "reactant" includes any substance that is present at the start of a chemical or biochemical reaction. In one embodiment, at least one fluid is a solvent, and at least one solute is mixed therewith.

In accordance with the present invention, a method of mixing three or more fluids inside a capillary comprises the steps of: (a) sequentially introducing the three or more fluids into the capillary by pressure injection, under conditions of laminar flow (e.g., non-turbulent fluid flow); and (b) allowing the fluids to mix inside the capillary by diffusion. As used herein, the term "pressure injection" refers to one of the basic methods for introducing a fluid into a capillary by differential pressure. As further used herein, "differential pressure" means the difference of pressures between ends of the capillary. For example, positive differential pressure may be applied to the injection end of the capillary (i.e., the end at which a fluid is introduced), for a sufficient amount of time, in order to push the fluid into the capillary. Alternatively, negative differential pressure may be applied to the non-injection (opposite) end of the capillary, to cause suction of the fluid into the capillary at the injection end.

In fluid dynamics, laminar flow is known to be a flow regime typically characterized by high-momentum diffusion, low-momentum convection, and pressure and velocity that are not dependent upon time. The (dimensionless) Reynolds number characterizes whether flow conditions lead to laminar or turbulent flow. Generally, laminar flow can be achieved by modulating one or more of the following parameters: transverse dimension of the flow (e.g., inner diameter of the capillary), pressure, temperature, and viscosity. Typically, it is difficult to create turbulent flow inside a capillary tube; thus, a person skilled in the art can readily obtain the conditions necessary to ensure laminar flow inside the capillary.

It is known in the relevant art that a particular volume of liquid introduced into a capillary may be referred to as a "plug". Accordingly, in the method of the present invention, each fluid may be introduced into the capillary as a plug of fluid. In one embodiment, the plug of fluid has, inside the capillary, a non-rectangular concentration profile corresponding to the shape of its concentration gradient. As disclosed herein, the non-rectangular concentration profile is generally parabolic in shape, with the vertex of the parabola moving longitudinally through the capillary, along its X axis. The "introduction time", as used herein, is the time required to introduce one volume of fluid into the capillary (i.e., it is the time that passes between the beginning and the end of introduction of a fluid). Preferably, each of the fluids is introduced into the capillary with an introduction time of less than 3 seconds; more preferably, the introduction time for each fluid is 1 second or less. Introduction time may be affected by any of a number of factors, including, without limitation, capillary inner diameter, injection plug volume, injection pressure-seconds, viscosity of fluid to be injected, and viscosity of fluid(s) previously injected.

Following introduction into the capillary, the three or more fluids are allowed to mix by diffusion inside the capillary. In certain embodiments, the three or more fluids comprise at least two reagents, such that a reaction occurs inside the capillary upon mixing. Accordingly, the method of the present invention may further comprise the step of separating reaction components (e.g., one or more unused reagents, one or more reaction products, etc.) inside the capillary. Separation of the reaction components may be accomplished, for example, by capillary electrophoresis, capillary chromatography, or any other small-volume separation techniques known in the art or later determined. In one embodiment, the step of separating reaction components comprises the step of detecting the reaction components during or following separation. The reaction components may be detected inside the capillary, or at one end of the capillary upon exiting therefrom, by absorbance, chemiluminescence, fluorescence, mass spectrometry, an electrochemical detector, etc.

By way of example, reagents used in the present invention may comprise at least one antigen and at least one antibody; at least one aptamer and at least one target thereof; at least one DNA-binding protein and at least one DNA; at least one RNA-binding protein and at least one RNA; at least one enzyme and at least one enzyme substrate; at least one ligand and at least one receptor; or at least one drug candidate and at least one therapeutic target. Accordingly, the method of the present invention may further comprise the step of screening for, detecting, and/or measuring binding (e.g., measuring parameters for binding) and/or interaction (e.g., activation, inhibition, modulation, etc.) between any two or more of the reagents inside the capillary. Parameters for binding parameters include, without limitation, rate constants, equilibrium constants, thermodynamic parameters, and stoichiometry of binding.

For example, where the reagents comprise at least one enzyme and at least one enzyme substrate, the method of the present invention may further comprise: (a) the step of screening for at least one enzyme-substrate complex; and/or (b) the step of screening for at least one enzyme inhibitor, including measuring inhibition efficiency of the at least one enzyme inhibitor. Where the reagents comprise at least one drug candidate and at least one therapeutic target (e.g., a protein), the method of the present invention may further comprise: (a) the step of detecting or measuring binding (e.g., measuring parameters for binding) of the drug candidate and the therapeutic target; and/or (b) the step of screening for at least one drug-target complex. The step of measuring binding may, for example, be associated with high-throughput screening for candidate drugs.

In accordance with the method of the present invention, it will now be possible to use a "plug-and-play" method for quantitative screening of large libraries of enzyme inhibitors by capillary electrophoresis (CE). The "plug-and-play" method involves injecting all reaction components into the capillary as separate "plugs", and reacting them inside the capillary in a way that requires no optimization. Conceptually, the capillary is pre-filled with a run buffer suitable for separating the substrate from the product. Every reaction component—substrate, inhibitor, and enzyme—is then injected into the capillary by pressure as a separate short plug; the inhibitor plug is preferably placed between the enzyme and substrate plugs. If the run buffer is different from an enzymatic buffer, plugs of the enzymatic buffer are injected prior to the first and after the last plugs of reaction components. In one embodiment, at least one buffer plug may be injected by electroosmotic flow. The reaction components are allowed to mix by diffusion and to react inside the capillary. Thereafter, the reaction product may be separated from the unreacted substrate by CE, and then quantified.

The amount of the product, as a function of the inhibitor concentration, may be used to determine the inhibition constant, $K_I$, of the inhibitor. An uncontrolled reagent dilution during in-capillary mixing may prevent direct determination of $IC_{50}$ values; therefore, an inhibitor with known $IC_{50}$ may be used as a standard reference to determine unknown $IC_{50}$ values accurately.

The plug-and-play method does not require premixing of reaction components outside of the capillary. Furthermore, the volumes of the injected plugs can be as low as 1 nanoliter. Thus, microliter volumes of the enzyme and substrate solutions will be sufficient for screening thousands of potential inhibitors. The plug-and-play method will be applicable to any enzymatic reaction after only minor optimization, provided that a suitable run buffer is utilized. Accordingly, it is expected that the plug-and-play method will provide a universal approach for identification and characterization of enzyme inhibitors; it will be a valuable addition to the arsenal of existing drug discovery methods.

In certain other embodiments of the present invention, the method may further comprise the step of optimizing (e.g., optimizing efficiency of) step (a) and/or step (b), by analyzing laminar flow profiles of the three or more fluids inside the capillary. By way of example, laminar flow profiles may be analyzed by a mathematical model that analyzes the shapes of profiles (e.g., parabolic profiles, as shown in FIG. 1) to calculate concentration profiles of mixed solutions (e.g., in a graph, as shown in FIG. 1). The method may be optimized, for example, by reducing the time required to introduce each plug of fluid into the capillary. This may be achieved, for instance, by increasing the pressure required for pressure injection, while ensuring that the pressure remains sufficiently low to avoid inducing turbulence. The optimizing step may include analyzing diffusion of the laminar flow profiles.

In one embodiment of the present invention, the laminar flow profiles are analyzed using various parameters, including, without limitation, a coefficient of diffusion of a molecule inside the capillary tube, a diameter of the capillary tube, a time of introduction of a fluid into the capillary tube, a time of incubation of a fluid inside the capillary tube, the number of fluids to be mixed inside the capillary tube, position of at least one fluid on an array of fluids to be mixed inside the capillary tube, molecular weight of at least one solute in at least one fluid to be mixed inside the capillary tube, viscosity of at least one fluid inside the capillary tube, viscosity of at least one fluid to be mixed inside the capillary tube, and/or volume of at least one fluid to be mixed inside the capillary tube. The optimizing step may also comprise use of a computer program, as described herein.

By way of example, the optimizing step of the present invention may comprise calculating concentration profiles (e.g., concentration gradient profiles) of the three or more fluids inside the capillary. Additionally, the optimizing step may comprise calculating rates of a chemical reaction (e.g., an enzymatic reaction) inside the capillary. The optimizing step may also comprise introducing a buffer into the capillary. As used herein, a "buffer" includes a fluid that does not contain solutes which are to be added to the buffer; this may also be referred to as a "blank buffer". Accordingly, in one embodiment of the present invention, the fluid is a liquid solvent or blank buffer, and at least one solute is mixed with this solvent. Additional exemplary buffers include, without limitation, pH buffers for aqueous reactions. Furthermore, the optimizing step may comprise introducing each of the three or more fluids into the capillary with an introduction time of less than 3 seconds; preferably, the introduction time for each fluid is 1 second or less.

The present invention further provides a method for optimizing efficient mixing of two or more (e.g., 2, 3, 4, 5, 6, 7, 8, etc.) fluids inside a capillary, comprising the step of analyzing laminar flow profiles of the two or more fluids inside the capillary. Also provided is a computer-readable medium having recorded thereon (e.g., as a computer program, software, etc.) statements and instructions for execution by a processor to carry out this method. The processor of the invention may comprise any one or more data processor(s), computer(s), and/or other system(s) or device(s). Moreover, the processor may comprise any necessary or desirable input/output, communications, control, operating system, and other devices, including software, suitable for accomplishing the purposes described herein. For example, a general-purpose data processor provided on one or more circuit boards (e.g., as provided by Intel, IBM, Compaq, and a number of other producers), using a UNIX, Apple, or Microsoft general-purpose operating system and suitable application software programs (including Excel), will suffice. A large number of suitable devices are now available, and will doubtless hereafter be conceived and developed. The selection of suitable components to serve as and/or with processors, including support and control components and software, in accordance with the invention, will be readily apparent to those of ordinary skill in the art, once they have been made familiar with this disclosure.

The present invention also provides a method for optimizing efficient mixing of two or more fluids inside a capillary, wherein the method is implemented by a computer comprising at least one processor. The optimizing method comprises: (a) receiving input in response to a user prompt, the input comprising at least one parameter of mixing (i.e., a condition, parameter, variable, etc. that is relevant to the optimization of efficient mixing of fluids inside a capillary); and (b) using the input to analyze laminar flow profiles of the two or more fluids inside the capillary. Exemplary parameters of mixing include, without limitation, a coefficient of diffusion of a molecule, a diameter of the capillary, a time of introduction of a fluid into the capillary, a time of incubation of a fluid inside the capillary, the number of fluids to be mixed, position of at least one fluid on an array of fluids, molecular weight of at least one solute in at least one fluid, viscosity of at least one fluid inside the capillary, viscosity of at least one fluid to be introduced into the capillary, and volume of at least one fluid. Additional factors that may be used as parameters include temperature, pressure delivery, the time required for pressure to rise and fall, etc. The user prompt may, for example, be presented at a user interface.

In one embodiment of the present invention, the analysis performed in step (b) uses an algorithm of mixing, or a procedure of mixing, comprising at least one optimized parameter of mixing. Examples of such optimized parameters include, without limitation, the parameters of mixing discussed above, as well as the number of fluids to be mixed inside the capillary tube, the order in which fluids are introduced into the capillary tube, the presence or the absence of a buffer plug inside the capillary tube, a time of introduction of a fluid into the capillary tube, a time of incubation (mixing) of a fluid inside the capillary tube, and a time of reaction of a chemical reaction inside the capillary tube. In another embodiment of the invention, the analysis in step (b) comprises calculating a concentration profile for at least one of the fluids inside the capillary. In a further embodiment, the analysis in step (b) comprises calculating at least one rate of a chemical reaction (e.g., an enzymatic reaction) inside the capillary. By way of example, the reaction may comprise formation of a complex (e.g., a complex comprising a protein and a candidate drug).

The present invention further provides an automated system for mixing two or more fluids inside a capillary in accordance with methods described herein. The automated system comprises: (a) a robot for inserting a capillary into at least one container (e.g., holder, plate, vial, etc.) housed within the system, the at least one container providing a source for two or more fluids to be introduced inside the capillary at a first end of the capillary; (b) pump means for applying a pressure change at the first end of the capillary, whereby a fluid in the at least one container may be introduced inside the capillary; (c) temperature control means for controlling temperature inside the capillary; and (d) a processor adapted to analyze laminar flow profiles of the two or more fluids inside the capillary, so as to optimize mixing of the two or more fluids inside the capillary. A capillary and at least one container may be added to the automated system when needed. Preferably, each of the two or more fluids is introduced into the capillary with an introduction time of 1 second or less.

The processor of the present invention, as described above, may be adapted to receive and process input parameters provided by a user. Relevant parameters include, without limitation, a coefficient of diffusion of a molecule inside the capillary tube, a diameter of the capillary tube, a time of introduction of a fluid into the capillary tube, a time of incubation of a fluid inside the capillary tube, the number of fluids to be mixed inside the capillary tube, position of at least one fluid on an array of fluids to be mixed inside the capillary tube, molecular weight of at least one solute in at least one fluid to be mixed inside the capillary tube, viscosity of at least one fluid inside the capillary tube, viscosity of at least one fluid to be mixed inside the capillary tube, and volume of at least one fluid to be mixed inside the capillary tube. In certain embodiments, the processor includes software comprising an algorithm of mixing. The algorithm may comprise at least one optimized parameter of mixing (e.g., the number of fluids to be mixed inside the capillary tube, the order in which fluids are introduced into the capillary tube, the presence or the absence of a buffer plug inside the capillary tube, a time of introduction of a fluid into the capillary tube, a time of incubation (mixing) of a fluid inside the capillary tube, and/or a time of reaction of a chemical reaction inside the capillary tube).

By way of example, the automated system of the present invention may be a standard capillary electrophoresis (CE) or capillary chromatography device that has been adapted for use in a method for mixing two or more fluids inside a capillary. Preferably, the automated system is capable of optimizing the mixing of two or more fluids inside a capillary (e.g., it can facilitate introduction of each fluid into the capillary by ensuring an introduction time of less than 3 seconds, and, preferably, 1 second or less). For example, the automated system of the invention may be a P/ACE™ 2000-5000 (Beckman Coulter; Fullerton, Calif.), P/ACE™ System MDQ (Beckman Coulter; Fullerton, Calif.), ProteomeLab™ PA 800 Protein Characterization System (Beckman Coulter; Fullerton, Calif.), or a generic CE (any other CE system) that has been modified to facilitate and optimize the mixing of two or more fluids inside a capillary.

In one embodiment, the automated system of the present invention further comprises at least one detecting device and/or separation device coupled to the capillary at, or near, a second end thereof. Exemplary detecting and/or separation devices include, without limitation, a device for detecting absorbance, a device for capillary electrophoresis, a device for capillary chromatography, a device for detecting chemiluminescence, a device for detecting fluorescence, a device for electrochemical detection, and a device for mass spectrometry.

The present invention is described in the following Examples, which are set forth to aid in the understanding of the invention, and should not be construed to limit in any way the scope of the invention as defined in the claims which follow thereafter.

EXAMPLES

Example 1

Physical Bases of TDLFP

In the present example, the inner diameter of the capillary is assumed to be 50 μm, and the length of every solution plug is assumed to be at least 30 times greater than this diameter. A characteristic time of longitudinal diffusion is at least 900 ($30^2$) times longer than that of transverse diffusion. This allows for a first simplifying assumption: longitudinal diffusion is negligible in TDLFP.

Crucial to TDLFP, a pressure-injected non-diffused plug has a parabolic profile (Hunter and Carta, *J. Chromatogr., A.,* 971:105-11, 2002; Sharma et al., *Anal. Chem.,* 77:806-13, 2005), due, at least in part, to friction along the walls of the capillary. Transverse diffusion during plug injection will affect the parabolic profile; however, shortening the injection time with respect to a transverse diffusion time can make this effect negligible. Indeed, a plug of solution a few millimeters in length can be injected into the capillary by high pressure within a fraction of a second, without disturbing the laminar nature of the flow (Kinzer et al., *Anal. Chem.,* 68:3250-257, 1996; Culbertson et al., *Anal. Chem.,* 66:955-62, 1994). Characteristic times of transverse diffusion in the capillary are greater than 1 second, even for small biomolecules such as amino acids; for biopolymers, such as proteins, transverse diffusion can take as long as a minute (McGuffin, V. L., *Electrophoresis,* 22:3709-711, 2001; Griffiths and Nilson, *Anal. Chem.,* 71:5522-529, 1999; Gas et al., *J. Chromatogr., A.,* 709:63-68, 1995). Thus, it is possible to inject a plug of solution with a virtually-undisturbed parabolic shape. To facilitate more general application, it is necessary to take into account the transverse diffusion during plug injection.

Injection of the second reagent requires replacement of the reservoir with a solution; this takes longer than 1 second. It is difficult to minimize this time; thus, the effect of diffusion during reservoir replacement on the plug profile can hardly be made negligible. Accordingly, a second simplifying assumption may be made: after every injection, the plugs inside the capillary are allowed to diffuse and eliminate concentration gradients in the transverse direction.

As discussed in Example 2, a simple mathematical model of TDLFP has been developed, based on the two above-described assumptions. The non-numerical nature of the model advantageously permits the use of Excel software for modeling TDLFP.

Example 2

Non-Numerical Mathematical Model of TDLFP

The general model of mass transfer aims at calculating concentrations of substances mixed by TDLFP as functions of the position in the capillary and time passed since the beginning of mixing. If the solution is injected in the capillary by differential pressure, mass transfer is described by the following equation system:

$$\frac{\partial n}{\partial t} = -v(r)\frac{\partial n}{\partial x} + \mu\left(\frac{\partial^2 n}{\partial x^2} + \frac{1}{r}\frac{\partial}{\partial r}r\frac{\partial n}{\partial r}\right) \quad (1)$$

$$v(r) = v_0(1 - (r/r_0)^2)$$

$$\mu\frac{\partial n}{\partial r}\bigg|_{r=r_0} = 0$$

wherein n is the concentration of the substance, μ is its diffusion coefficient, v is its velocity along the axis of the capillary, r is the distance from an axis of a capillary, x is the distance from the injection end of the capillary, t is time from the beginning of injection, $r_0$ is the radius of the capillary, and $v_0$ is the velocity of the substance along the axis of the capillary for r=0.

If it is assumed that the characteristic length of the injected plug, L, is much greater than the diameter of the capillary, the time required for transverse diffusion, $t_r$, is much shorter than the time required for longitudinal diffusion, $t_x$:

$$t_r \sim r_0^2/\mu, \; t_x \sim L^2/\mu$$

$$t_x/t_r \sim L^2/r_0^2 \quad (2)$$

This permits the mixing by longitudinal diffusion to be ignored, thereby allowing the top equation in system (1) to be simplified as follows:

$$\frac{\partial n}{\partial t} = -v(r)\frac{\partial n}{\partial x} + \mu + \frac{1}{r}\frac{\partial}{\partial r}r\frac{\partial n}{\partial r} \quad (3)$$

$$v(r) = v_0(1-(r/r_0)^2)$$

$$\mu\frac{\partial n}{\partial r}\bigg|_{r=r_0} = 0$$

Although system (3) provides the general basis for modeling plug formation, its analytical solution is difficult. Solving this equation analytically becomes feasible, however, if either of the two terms at the right-hand side of the top equation in system (3) is negligible with respect to the other one. In other words, the analytical solution of system (3) can be found if either the coefficient of diffusion or the velocity can be assumed to be zero. Both assumptions were used in the present modeling: it was assumed that diffusion is negligible during injection, and it was assumed that velocity is zero during mixing. Turning off the differential pressure easily satisfies the second assumption. This assumption simplifies system (3) to:

$$\frac{\partial n}{\partial t} = -v(r)\frac{\partial n}{\partial x} \quad (4)$$

$$v(r) = v_0(1-(r/r_0)^2)$$

System (4) has a general solution:

$$n = F(x-tv(r)) \quad (5)$$

If the plug is injected from a vial, in which the concentration of the substance is $n_0$, the distribution of the substance concentration in the capillary is described by the following equation:

$$n(t,x,r) = n_0\theta(x-tv_0(1-(r/r_0)^2)) \quad (6)$$

Here, $\theta(x)$ is a function which equals 1 if $x>0$, and otherwise equals 0. This function allows the distribution of the substance in the capillary to be described, not only after the injection, but also prior to it ($t<0$). According to equation (6), if $t<0$, the concentration of the substance inside the capillary ($x>0$) is 0, while, on the interface between the capillary and the solution in the vial ($x=0$), the concentration of the substance is equal to that in the vial. According to equation (6), the profile of the injected plug is parabolic, as depicted in FIG. 1.

Inside the capillary, the concentration equals to $n_0$ within the plug, and equals to 0 outside the plug. Knowing the form of plug permitted the inventors to calculate the average concentration for each section of a capillary:

$$N(x) = \frac{2}{r_0^2}\int_0^{r_0} n(t, x, r)r\,dr \quad (7)$$

In particular, for the parabolic distribution described by equation (6), the average "per-section" concentration is:

$$N(x) = n_0\theta(x-tv_0)(x/tv_0-1) \quad (8)$$

Figure 3:
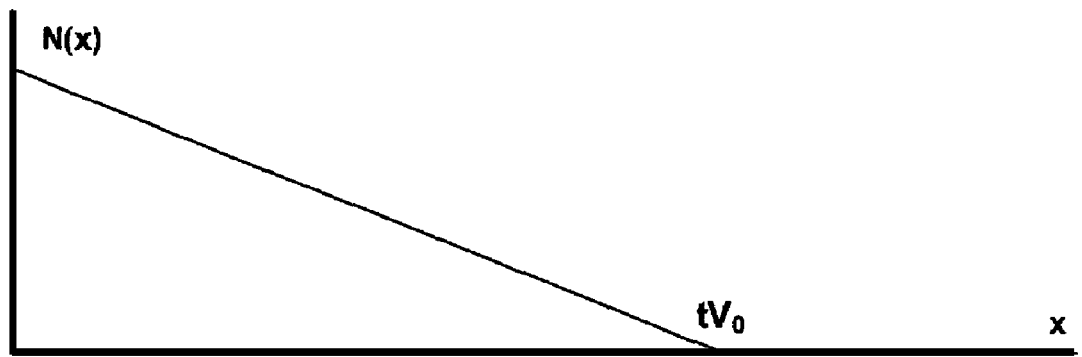
FIG. 3 depicts the linear x-profile, for the fixed time, t, of the concentration of a fluid having a parabolic distribution inside a capillary. N(x) (Y axis) shows the average concentration, and x (X axis) shows distance from the first end of the capillary.

The x-profile of this distribution for the fixed t is linear, as shown in FIG. 3.

Generally, the inventors injected multiple plugs of different substances into the capillary. After every injection, the injected substances were allowed to diffuse into each other for a period of time that was longer than $t_r$ and shorter than $t_x$. As a result, gradients in the direction perpendicular to the capillary axis (x) were eliminated for all injected plugs. If it is assumed that the resulting x-profile of plug number j is described by a function $N_j(x)$, the distribution of plug j will become non-uniform after injecting plug number j+1, with time of injection t:

$$n(t,x,r) = N_j(x-v_0(1-(r/r_0)^2)t) \quad (9)$$

This equation is obtained from the general solution represented by equation (5).

If equation (9) is substituted into equation (7), it is possible to obtain the distribution of the concentration for plug j+1 on x after time of injection $t_{j+1}$:

$$N_{j+1}(x) = 2\cdot\int_0^{r_0} N_j(x-v_0(1-(r/r_0)^2)t_{j+1})r\,dr/r_0^2 \quad (10)$$

Equation (10) can then be transformed to:

$$N_{j+1}(x) = \int_{x-t_{j+1}\cdot v_0}^{x} N_j(z)dz/(t_{j+1}\cdot v_0) \quad (11)$$

where $z = x - v_0(1-(r/r_0)^2)t_{j+1}$. The last equation sets the iterative procedure, which allowed the inventors (by means of repetitive integration) to determine final distributions of substances in all injected plugs. In particular, using as $N_1$ the distribution determined from equation (8), and substituting it into the right part of equation (11), it was possible to calculate analytically the corresponding integral, to receive $N_2$, then to find analytical expression for $N_3$, and so on.

Example 3

Application of Non-Numerical Mathematical Model to Simulate TDLFP-based Mixing

FIG. 1 illustrates simulated mixing of two reagents, blue and red, in several steps, with gradually-increasing spatial overlap of the reagents. For clarity of this schematic consideration, transverse diffusion during plug injection will be neglected.

In step 1, a parabolic plug of the blue solution is injected. Transverse diffusion of the parabolic profile eliminates the concentration gradient in the transverse direction. The resulting concentration profile of the blue component is linear. In step 2, the same volume of the red solution is injected. Parabolic profiles of both plugs are established, with the interface between them being predominantly in the longitudinal direction. Transverse diffusion of the parabolic profiles, which follows the injection, eliminates the concentration gradients in the transverse direction, and mixes the blue and the red solutions. The mixing zone has a length equal to that of the red plug. The concentration profiles of the blue and red components are not similar; overall, 100% of the red component, and approximately 50% of the blue component, are mixed.

In step 3, the second blue plug of the same volume is injected, and mixed with the two plugs that were previously injected. The concentration profiles are still not similar, but approximately 100% of the two components are mixed. In step 4, a plug of buffer is injected, and mixed with the first three plugs. The buffer plug has a volume equal to the total volume of the first three plugs. Remarkably, the resulting concentration profiles are almost identical.

In the resulting reaction mixture, the blue and red components are diluted by factors of approximately three and six, respectively. In accordance with this method, more than two components can be mixed in a similar way.

Examples 4-8 summarize the materials and methods used in connection with the experiments of Example 9:

Example 4

Materials

β-galactosidase (β-Gal) (isolated from *E. coli*), fluorescein mono-β-D-galactopyranoside (FMG), and fluorescein sodium salt were purchased from Sigma-Aldrich (Oakville, ON, Canada). All other chemicals were from Sigma-Aldrich, Caledon, or BDH (Toronto, ON, Canada), and were of analytical grade. Stock solutions of 4.4 mM FMG and 5 nM β-Gal were prepared with 10 mM phosphate (pH 7.2) buffer containing 1 mM $MgCl_2$, and stored at −80° C. The 10 nM phosphate (pH 7.2) buffer containing 1 mM $MgCl_2$ was also used for enzyme reactions, and for capillary electrophoresis as a run buffer. All solutions were made using Milli-Q-quality de-ionized water filtered through a 0.22 μm filter (Millipore; Nepean, ON, Canada).

Example 5

Capillary Electrophoresis

All capillary electrophoresis (CE) experiments were carried out with a P/ACE MDQ instrument equipped with a laser-induced fluorescent (LIF) detector (Beckman-Coulter; Fullerton Calif.). Fluorescence was excited by a 488-nm line of an argon-ion laser (5 mW). Fluorescent light was filtered through a band pass filter cantered at 520 nm. Uncoated fused-silica capillaries (Polymicro; Phoenix, Ariz.) with the following dimensions were used: 50-cm length; 40-cm length from the injection end to the detector; 50-μm inner diameter; and 365-μm outer diameter. New capillaries were pre-treated with 1 M NaOH for 60 min, followed by pumping water for 60 min at room temperature. Prior to every run, the capillary was rinsed with the run buffer for 2 min. At the end of each run, the capillary was rinsed with 0.1 M HCl and 0.1 M NaOH for 2 min, each followed by a rinse with de-ionized water for 2 min.

Example 6

Offline Enzyme Reaction

6 μL of 1 μM FMG, 3 μL of 1 nM β-Gal, and 9 μL of 10 mM phosphate buffer containing 1 mM $MgCl_2$ were mixed in a 200 μL reservoir. The mixture was capped, vigorously mixed, centrifuged briefly at 8000×g, and allowed to incubate at 25° C. for a period of time ranging from 5 min to 65 min. The reaction mixture was directly used for quantifying the amount of the product by CE. Sample introduction was performed by hydrodynamic injection at 0.5 p.s.i. for 6 seconds. The applied voltage for the CE separation was 25 kV. The identification and quantitative assay of products were preformed by the addition of fluorescein (internal reference) to the reaction mixture.

Example 7

TDLFP Mixing and Enzymatic Reaction

The injection sequences were as follows:
for 2-step mixing: FMG solution (0.5 p.s.i.; 3 seconds) and β-Gal solution (0.5 p.s.i.; 3 seconds), with mixing for 1 min;
for 3-step mixing: FMG solution (0.5 p.s.i.; 3 seconds), β-Gal solution (0.5 p.s.i.; 3 seconds), and FMG solution (0.5 p.s.i.; 3 seconds), with mixing for 1 min; and
for 4-step mixing: FMG solution (0.5 p.s.i.; 3 seconds), β-Gal solution (0.5 p.s.i.; 3 seconds), FMG solution (0.5 p.s.i.; 3 seconds), and buffer (0.5 p.s.i.; 9 seconds), with mixing for 1 min.

After each injection of FMG or β-Gal, the capillary and electrode were dipped in the enzymatic buffer, in order to prevent the contamination of solutions from which the next plugs were to be injected. To allow the enzymatic reaction to proceed, the reaction mixtures were incubated for periods of time ranging from 3 min to 40 min. Thereafter, a voltage of 25 kV was applied to stop the reaction, to separate the product from the substrate, and to detect the amounts of the remaining substrate and formed product. The amount of the product was quantified as described above.

Example 8

Determination of $K_M$ and $K_{CAT}$

The $K_m$ and $K_{cat}$ values were determined using an approach previously described by Berezovski et al. (*Electrophoresis*, 23:3398-403, 2002). Briefly, a series of solutions with different concentrations of FMG were used in the offline enzyme reaction when the incubation time was 35 min; other conditions were similar to those described above. The values of $K_m$ and $K_{cat}$ were calculated using the Michaelis-Menten equation.

Example 9

Experimental Results of Simulated Mixing

The inventors experimentally examined the results of the simulated mixing, using materials described in Examples 4-8 above. In a manner similar to that illustrated in FIG. 1, the inventors mixed an enzyme, β-galactosidase, with its fluorescently-labeled substrate, fluorescein-mono-β-D-galactopyranoside. The 4 plugs were introduced in the following order: substrate, enzyme, substrate, buffer. After mixing, the enzymatic reaction was allowed to proceed for varying periods of time. The reaction was stopped by electrophoretically separating the enzyme from the substrate; the product was also separated from the unreacted substrate electrophoretically. The quantity of the product was measured with a fluorescence detector, at the distal end of the capillary.

It was determined that the enzymatic reaction proceeded in time- and concentration-dependent fashions, thereby confirming that the reagents were mixed by TDLFP. Next, experimental reaction kinetics were compared with kinetics predicted by the mathematical model of TDLFP. The simulated kinetics were calculated by integrating product formation along the capillary length. The model used the values of the catalytic rate constant, $k_{cat}=0.6$ $s^{-1}$, and the Michaelis constant, $K_m=0.9$ μM, which were determined in a separate experiment by mixing the reaction components in a vial.

Figure 2:
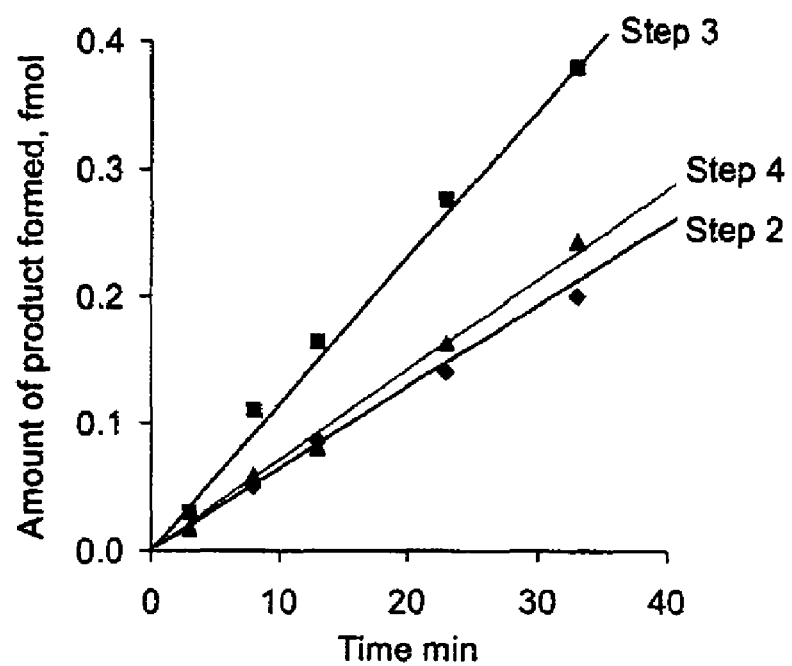
FIG. 2 illustrates a graph of product versus time. Simulated (lines) and experimental (dots) kinetics of enzymatic glycosylation of fluorescein-mono-β-D-galactopyranoside are depicted. The enzyme and the substrate were mixed by transverse diffusion of laminar-flow profiles (TDLFP), using the procedure shown in FIG. 1.

FIG. 2 compares simulated and experimental reaction kinetics. To generate comprehensive data, this comparison was done for the 2-, 3-, and 4-step mixing procedures described in FIG. 1. Remarkably, the experimental reaction rates were in perfect agreement with the predicted ones for the three mixing steps. This demonstrates that TDLFP can mix reagents inside the capillary; it also demonstrates that reagents can be mixed in a fully predictable fashion.

Example 10

Study of the "Plug-and-Play" Method

Using a "plug-and-play concept" (which involves injecting all reaction components into a capillary as separate "plugs", and reacting them inside the capillary in a way that requires no optimization), the inventors examined inhibition of farnesyl transfer from farnesyl pyrophosphate to a fluorescently-labeled peptide (Gly-Cys-Val-Ilu-Ala) catalyzed by protein farnesyltransferase (PFTase)—a target for mechanism-based anticancer therapies. Since this study involved a 2-substrate reaction, the inventors used 5 consecutive plugs—FPP, inhibitor, enzyme, inhibitor, and peptide—to satisfy the requirement that the inhibitor be placed between the enzyme and the substrate.

The inventors determined that, despite the relatively large total length of the 5 plugs (approximately 40 mm), TDLFP mixing was efficient enough for the reaction to proceed in concentration- and time-dependent fashions. As the inventors anticipated, the apparent $IC_{50}$ values exceeded the actual ones, due to reagent dilution during in-capillary mixing. To resolve this, the inventors introduced a "reference inhibitor" approach, in which an inhibitor with known $IC_{50}$ was used to find the correction coefficient, and the correction coefficient was then used to calculate the $IC_{50}$ of unknown inhibitors. Unexpectedly, the correction coefficient was relatively low (approximately 2.5±0.5). This suggests that, even without a reference inhibitor, the plug-and-play method can provide good estimates of $IC_{50}$.

Examples 11-15 discuss the development of a universal model for TDLFP.

Example 11

General Approach to Modeling of TDLFP-Assisted Mixing

Figure 4:
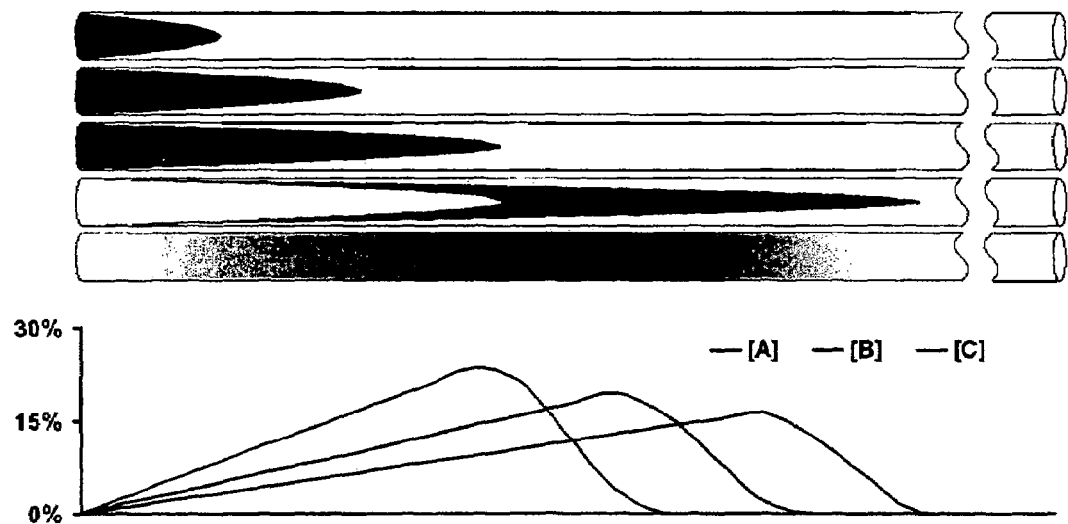
FIG. 4 presents a multi-stage process of hydrodynamic injection of three components, A (red), B (blue), and C (green). For simplicity, diffusion processes during injection are not taken into account, due to the small time required for injection. The figure shows filling of the initial region of the capillary at various stages. Step by step, in equal volumes, the following are injected: substance A, then substance B, then substance C, and, finally, a three-times-larger volume of buffer. The total distribution of substances A, B, and C, with respect to capillary length, are presented in the graph below.

The general idea of hydrodynamic mixing of components directly in a capillary, without use of any additional vials and devices, is illustrated in FIG. 4. In every injection, fluid, penetrating into the capillary, forms a needle-like structure, deeply infiltrating through the capillary axis in the solvent that was previously formed in the capillary. Upon completion of injections, the successively-formed layered structure diffuses relatively slowly down the length of the capillary, while a uniform distribution within every capillary cross-section is achieved much more quickly. This stage of the diffusion process is shown in the last fragment of FIG. 4.

The general model of mass transfer aims at calculating concentrations of substances mixed by TDLFP as functions of the position in the capillary and time passed since the beginning of mixing. If a solution is injected into a capillary by differential pressure, mass transfer is described by the following equation:

$$\frac{\partial n}{\partial t} = -v(r)\frac{\partial n}{\partial x} + \mu\left(\frac{\partial^2 n}{\partial x^2} + \frac{1}{r}\frac{\partial}{\partial r}r\frac{\partial n}{\partial r}\right) \quad (12)$$

$$v(r) = v_0(1-(r/r_0)^2)$$

$$\mu\frac{\partial n}{\partial r}\bigg|_{r=r_0} = 0.$$

Here, n is the concentration of the substance, μ is the diffusion coefficient, r is the distance from the axis of the capillary, x is the distance from the injection onset of the capillary, t is time from the beginning of injection, $r_0$ is the radius of the capillary, and v is the injection rate of the substance along the axis of the capillary, for r=0.

It is assumed that the characteristic length of the injected plugs, L, is related to injection time, T, by the equation $L=Tv_0$, where $v_0$ is the injection velocity along the axis of the capillary, is much greater than the diameter of the capillary. In this case, the time required for transverse diffusion, $t_r$, is much shorter than the time required for longitudinal diffusion, $t_x$:

$$t_r \sim r_0^2/\mu, \; t_x \sim L^2/\mu$$

$$t_x/t_r \sim L^2/r_0^2 \quad (13)$$

Thus, mixing by longitudinal diffusion may be neglected, and the top equation in system (12) may be simplified:

$$\frac{\partial n}{\partial t} = -v(r)\frac{\partial n}{\partial x} + \mu\frac{1}{r}\frac{\partial}{\partial r}r\frac{\partial n}{\partial r} \quad (14)$$

$$v(r) = v_0(1-(r/r_0)^2)$$

$$\mu\frac{\partial n}{\partial r}\bigg|_{r=r_0} = 0.$$

The above equation, conceived of by Taylor (Taylor, G., Dispersion of soluble matter in solvent flowing slowly through a tube. *Proceedings of the Royal Society of London*, Series A, Mathematical and Physical Sciences, 219(1137): 186-203, 1953), assumes some conversions of similarity. In particular, to reduce the equation to a standard dimensionless equation, the following variables may be introduced:

$$\rho=r/r_0, \; \chi=x/L, \; \tau=tv_0/L. \quad (15)$$

In these variables, equation (14) will become:

$$\frac{\partial n}{\partial \tau} = -(1-\rho^2)\frac{\partial n}{\partial \chi} + Yo\frac{1}{\rho}\frac{\partial}{\partial \rho}\rho\frac{\partial n}{\partial \rho} \quad (16)$$

$$\frac{\partial n}{\partial \rho}\bigg|_{\rho=1} = 0$$

where a dimensionless value is introduced $$Yo=\mu L/(v_0 r_0^2)=\mu T/r_0^2. \quad (17)$$

This important value is referred to herein as the "York number".

If there is a similarity of initial boundary conditions, then processes with the same York number will proceed in the same manner, no matter how the absolute values of the parameters differ. The York number may be represented by two dimensionless values, known in the relevant art (i.e., the art pertaining to the similarity of processes in fluid) as the Schmidt number (Sc=η/μ) and the Reynolds number (Re=$r_0 v_0/\eta$), where, through η, the kinematic viscosity of fluid is assigned, resulting in dimensionless ratio, $L/r_0$: Yo=L/(Sc Re $r_0$). Furthermore, it is possible to represent the York number in terms of the Peclet number, Pe=$Lv_0/\mu$, resulting in dimensionless ratio, $L/r_0$: Yo=L/(Pe $r_0$).

Table 1 presents values of Yo for sample cases (where time (T)=5 sec).

TABLE 1

Sample Yo values.

| $r_0$, cm | μ, cm²/s | | | | | |
|---|---|---|---|---|---|---|
| | 1.E-04 | 1.E-05 | 1.E-06 | 1.E-07 | 1.E-08 | 1.E-09 |
| 0.0025 | 80 | 8 | 0.8 | 0.08 | 8.E-03 | 8.E-04 |
| 0.00375 | 40 | 4 | 0.4 | 0.04 | 4.E-03 | 4.E-04 |
| 0.005 | 20 | 2 | 0.2 | 0.02 | 2.E-03 | 2.E-04 |

Example 12

Numerical Modeling of TDLFP-Assisted Mixing

Although system (16), above, provides the general basis for modeling plug formation, its analytical solution is difficult. Solving this equation analytically becomes feasible, however, if either of the two terms at the right-hand side of the top equation in system (16) is negligible with respect to the other. In the other words, the analytical solution of (16) can be found if either the coefficient of diffusion or the velocity can be assumed to be zero (Taylor, G., Dispersion of soluble matter in solvent flowing slowly through a tube. *Proceedings of the Royal Society of London*, Series A, Mathematical and Physical Sciences, 219(1137):186-203, 1953), or, more precisely, if the York number is much smaller than 1. Unfortunately, in a number of cases, it is not possible to neglect transverse diffusion.

Diffusion in the injection process is capable of reducing the effectiveness of the mixing of components, since it interferes with the deep penetration of injected components with respect to the capillary axis. Numerical modeling can take into account, quantitatively, the influence of diffusion on the process of injection.

For the purposes of numerical modeling, equations were presented in the form $$\frac{\partial n}{\partial \tau} = -(1-u)\frac{\partial n}{\partial \chi} + 4Yo\frac{\partial}{\partial u}u\frac{\partial n}{\partial u}, \quad (18)$$

$$\left.\frac{\partial n}{\partial u}\right|_{u=0} = 0, \left.\frac{\partial n}{\partial u}\right|_{u=1} = 0.$$

where the relationship u=ρ² is introduced. In the numerical modeling of system (18), it is necessary to take into account that solutions may be non-smooth for small coefficients of diffusion. Thus, the inventors selected an algorithm that gives no distortion at the zero level of diffusion.

The iteration of the computational procedure consisted of two sub-iterations. In the first sub-iteration, the inventors modeled the process of longitudinal shift of the fluid caused by the pressure; in the second sub-iteration, the process of transverse diffusion was modeled. The first sub-iteration was designed so that, after a given number of iterations, it would be possible to compensate for the mistake of modeling shifts of the capillary axis. For the second sub-iteration, a resistant scheme was chosen. The resulting computational scheme for a uniform 3-D grid of T, Y, and U, with the steps Δt, Δy, and Δu, and sizes ranging from zero to $\tilde{T}$, $\tilde{Y}$, and $\tilde{U}$, respectively, is:

$$n_{Y+Dy_{T,U},U}^{T+1/2} = n_{Y,U}^T$$

$$(n_{Y,U}^{T+1} - n_{Y,0}^{T+1/2})/\Delta t = (2Yo/\Delta u^2)(n_{Y,1}^{T+1} - n_{Y,0}^{T+1})$$

$$(n_{Y,U}^{T+1} - n_{Y,U}^{T+1/2})/\Delta t = (4Yo/\Delta u^2) \quad (19)$$

$$((U+\tfrac{1}{2})n_{Y,U+1}^{T+1} + (U-\tfrac{1}{2})n_{Y,U-1}^{T+1} - (2U+1)n_{Y,U}^{T+1}),$$
$$0 < U < \tilde{U}$$

$$(n_{Y,\tilde{U}}^{T+1} - n_{Y,\tilde{U}}^{T+1/2})/\Delta t = (4Yo/\Delta u^2)(\tilde{U}-\tfrac{1}{2})(n_{Y,\tilde{U}-1}^{T+1} - n_{Y,\tilde{U}}^{T+1})$$

where shifts along the capillary axis, $Dy_{T,U}$, are calculated using algorithm:

$$Dy_{T,U} = \text{round}\left(\left((1-U\Delta u)T\Delta t - \sum_{T'=0}^{T'=T-1} Dy_{T',U}\right)/\Delta y\right). \quad (20)$$

System (20) uses the function of rounding to the nearest natural number, round. Variables for system (18) are connected with discrete variables from systems (19) and (20) through the following ratios:

$$\tau = T\Delta t, \chi = Y\Delta y, u = U\Delta u \quad (21)$$

and the equality:

$$\tilde{U}\Delta u = 1 \quad (22)$$

is satisfied.

Example 13

Modeling of TDLFP-Assisted Mixing for Three-Substance Injection (Long Inter-Injection Time)

To illustrate the features of the technology of mixing described herein, the inventors set forth below the results of calculations for variations in the method of mixing three substances in a capillary microreactor. For this Example, it is assumed that injections are rapid and the delays between injections, in contrast to those in FIG. 4, are relatively large; thus, during transverse diffusion, there is time to create a complete uniformity in a cross-section of the capillary. Under these conditions, the presence of diffusion in the process of injection interferes with the efficient cross-penetration of mixed substances. Due to diffusion, an injected substance moves away from the axis of capillary and diffuses to the capillary walls, where hydrodynamic speed is small.

To model the mixing of three substances, the following scenario is assumed. In the first stage, substance A, 100% concentration, is injected for a short standard time, T. Thereafter, there is a period of time between injections that is long enough to permit the formation of a homogeneous distribution by sections. Substance B, 100% concentration, is then injected for time T. After a delay, substance C, 100% concentration, is injected for time T. In the final stage, after another delay, a buffer is injected for time NT, where N is a number which is typically greater than 1. (In the numerical experiments discussed below, N was N=12 or N=21). This final injection plays the role of mixer, increasing the uniformity of the mixing of components along the capillary axis. In the last numerical experiment, the time of buffer injection was 21T. For a high coefficient of diffusion, corresponding to Yo=8, the value 12T for time of final buffer injection is not sufficient for efficient mixing. The dynamics of the modeled injections are presented in Table 2.

TABLE 2

Dynamics of injection.

| | Duration of Injection | | | |
|---|---|---|---|---|
| | T | T | T | N × T |
| Substance | A | B | C | buffer |
| Relative Initial Concentration | 100% | 100% | 100% | 100% |

Figure 5:
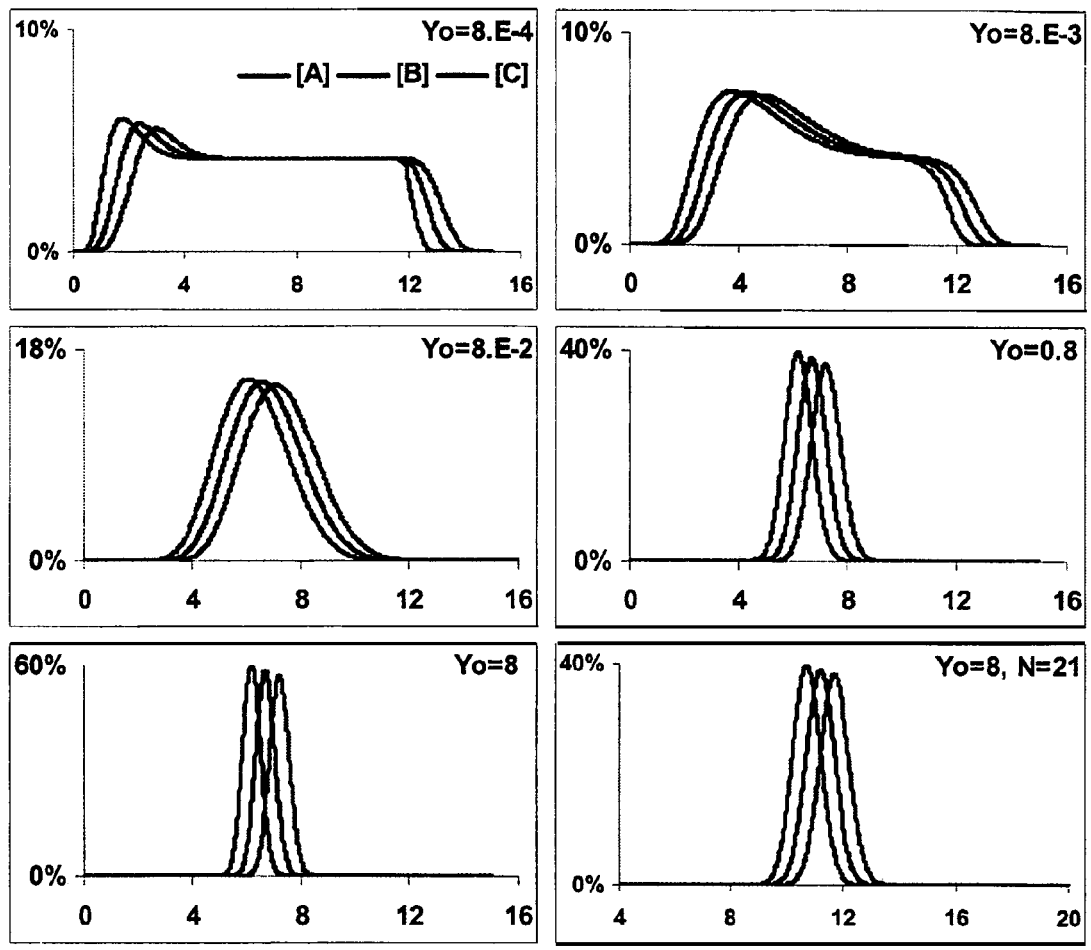
FIG. 5 sets forth the results of numerical modeling of final total distributions of three injected substances, A (red), B (blue), and C (green), with respect to capillary length. The abscissa axis represents units of shortest length of plugs used. The initial concentration of every substance, measured by the ordinate axis, is 100%.

According to simulated results, as shown in FIG. 5, a rather high uniformity of mixing can be achieved for low coefficients of diffusion. With increasing coefficients of diffusion, the uniformity of mixing decreases. However, in these cases, uniformity of mixing may be increased in a number of ways, including, for example: (a) by increasing the duration of the last buffer injection; or (b) by the proportional decrease in the duration of all injections (e.g., a ten-fold decrease in duration to simulate a ten-fold decrease in the coefficient of diffusion). In addition, the role of diffusion decreases with an increase in the radius of the capillary: a two-fold increase in the area of the capillary channel is proportional to a two-fold decrease in the diffusion coefficient.

Figure 6:
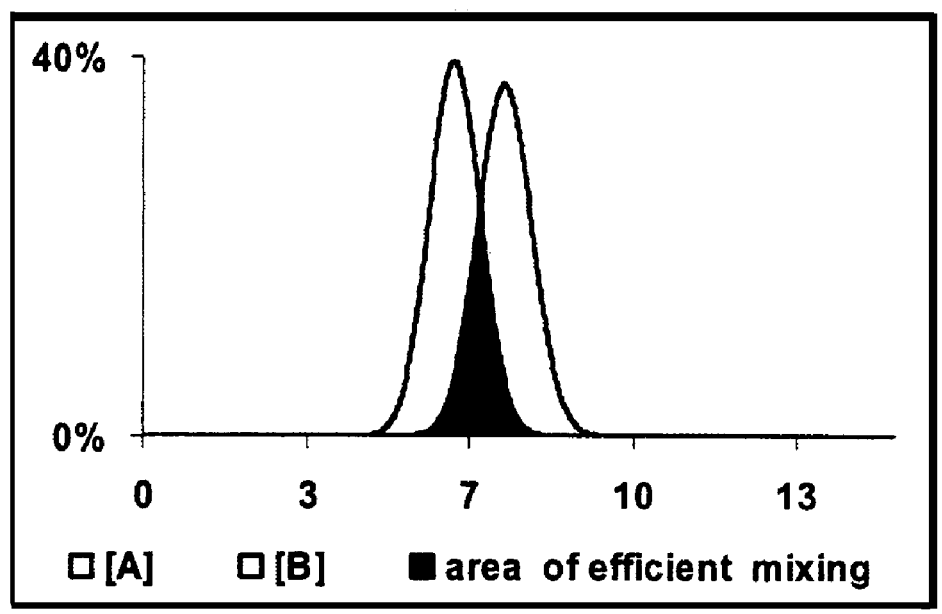
FIG. 6 illustrates the principle of estimating mixing efficiency, for the case of mixing two substances, A (red) and B (green).

The relative amount of components (with respect to the total amount) that can react after mixing can be used as a possible quantitative criterion of the level of mixing. In the present case, this requires an estimate of the ratio of the sum of minimum concentrations of all consumed substances, at every point, to the sum of maximum concentrations of all consumed substances that took part in the reaction. The principle of estimating mixing efficiency, for the case of mixing two substances, A and B, is illustrated in FIG. 6. For the above numerical experiments, the efficiencies of mixing three substances—A, B, and C—are shown in Table 3.

TABLE 3

Efficiencies of mixing three substances.

| | N | | | | | |
|---|---|---|---|---|---|---|
| | 12 | 12 | 12 | 12 | 12 | 21 |
| Yo | 0.0008 | 0.008 | 0.08 | 0.8 | 8 | 8 |
| Efficiency of mixing | 89% | 86% | 70% | 34% | 14% | 33% |

According to Table 3, for a low Yo value, the mixing of substances is close to 100%. For a larger Yo value, the level of mixing significantly decreases, but this may be partially compensated for by expanding the time of the mixing injection (i.e., the last injection of buffer).

There are a number of ways to increase the efficiency of mixing for large Yo values. For example, it is possible to increase the duration of the last mixing injection. For a long-lasting injection, the final substance plug can be injected far from the inlet of capillary. It is also possible to add an additional step: a pressure-driven shift of the reaction mixture in the opposite direction, which is driven by pressure applied to the distal end of the capillary. This changing of the direction of movement is analogous to shaking. For improved mixing, it is also possible to inject each substance twice, at half of its concentration. After TDLFP mixing, such a "multilayer sandwich" represents a good mixture structure of plugs. This approach is illustrated in FIG. 7 and in Tables 4 and 5 below.

TABLE 4

Figure 7:
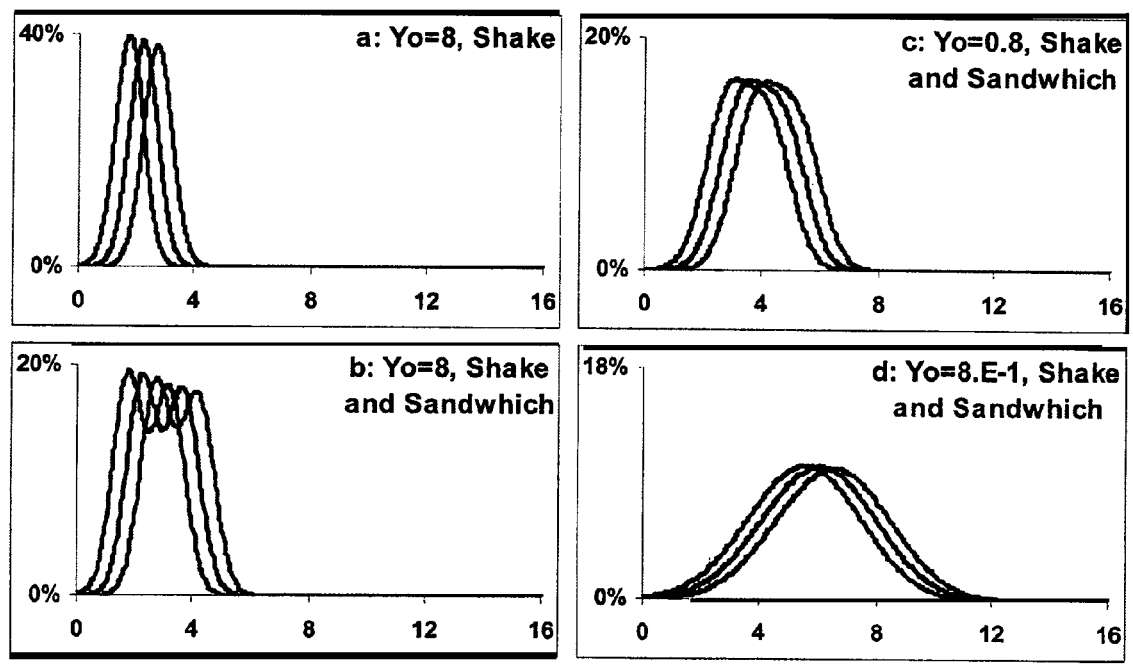
FIG. 7 depicts the creation of a "multilayer sandwich" by injecting each of three substances, A (red), B (blue), and C (green), at half-concentration.

Summary of results shown in FIG. 7, panel a.

| | Duration of Injection | | | | |
|---|---|---|---|---|---|
| | T | T | T | 12T | 9T |
| Substance | A | B | C | buffer | reverse pressure |
| Relative Initial Concentration | 100% | 100% | 100% | 100% | |

TABLE 5

Summary of "sandwich injections" shown in FIG. 7, panels b, c, and d.

| | Duration of Injection | | | | | | | |
|---|---|---|---|---|---|---|---|---|
| | T | T | T | T | T | T | Tb | Tr |
| Substance | A | B | C | A | B | C | buffer | reverse pressure |
| Relative Initial Concentration | 50% | 50% | 50% | 50% | 50% | 50% | 100% | |

Duration of mixing injection, Td, and reverse pressure period, Tr, are 12T and 9T, respectively, for the scenario depicted in FIG. 7, panel b; 13T and 8T, respectively, for the scenario depicted in FIG. 7, panel c; and 14T and 7T, respectively, for the scenario depicted in FIG. 7, panel d.

The efficiencies of mixing for "sandwich injections" are depicted in Table 6.

TABLE 6

Efficiencies of mixing for "sandwich injections".

| a), Yo = 8 | 33% |
|---|---|
| b), Yo = 8 | 62% |
| c), Yo = 0.8 | 68% |
| d), Yo = 0.08 | 80% |

According to Table 6, the efficiency is sufficiently greater for the mixing of sandwich injections than it is for the simpler variant of injections (shown in Table 3), even for the case of large York numbers.

Example 14

Modeling of TDLFP-Assisted Mixing for Four-Substance Injection

The present Example shows the application of the above-described numerical model in situations where the coefficients of diffusion, and, accordingly, the York numbers, for various injected substances do not coincide. The number of reacted components can be more than three. For example, the inventors describe herein the case of a two-substance enzymatic reaction that also involves an inhibitor. For both of the substrates, and the inhibitor, the diffusion coefficient is approximately $3\times10^{-6}$ cm$^2$/s; the diffusion coefficient for the enzyme is slightly smaller, at approximately $3\times10^{-7}$ cm$^2$/s. The dynamics of the modeled injection presented in Table 7.

TABLE 7

Dynamics of four-component mixing.

| | Duration of Injection | | | | |
|---|---|---|---|---|---|
| | T | T | T | T | 12T |
| Substance | Enzyme | Inhibitor | Substrate 1 | Substrate 2 | Buffer |
| Relative Initial Concentration | 50% | 50% | 50% | 50% | 100% |

For time T, there were two variants, corresponding to fast (T=3 sec) and slow (T=30 sec) injections. Additionally, for the slow injection, a slightly lower pressure was used. The radius of the capillary was 0.0025 cm.

Figure 8:
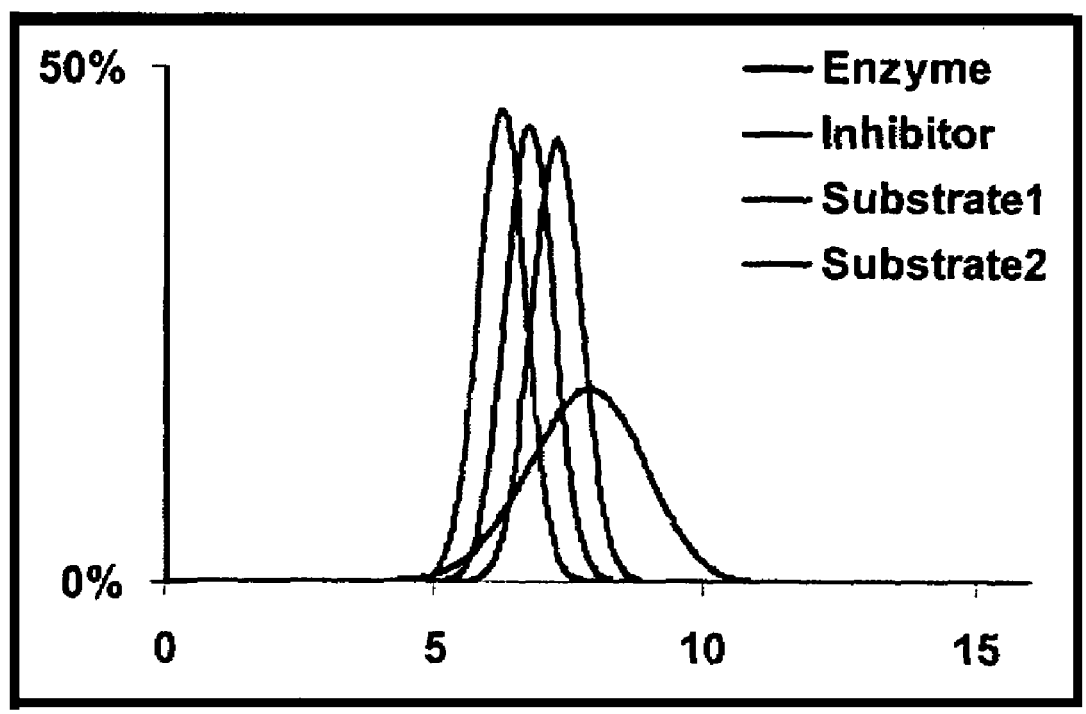
FIG. 8 presents the results of numerical modeling for fast injections, showing final total distributions with respect to capillary length. enzyme=red; inhibitor=black; substrate 1=blue; substrate 2=green
Figure 9:
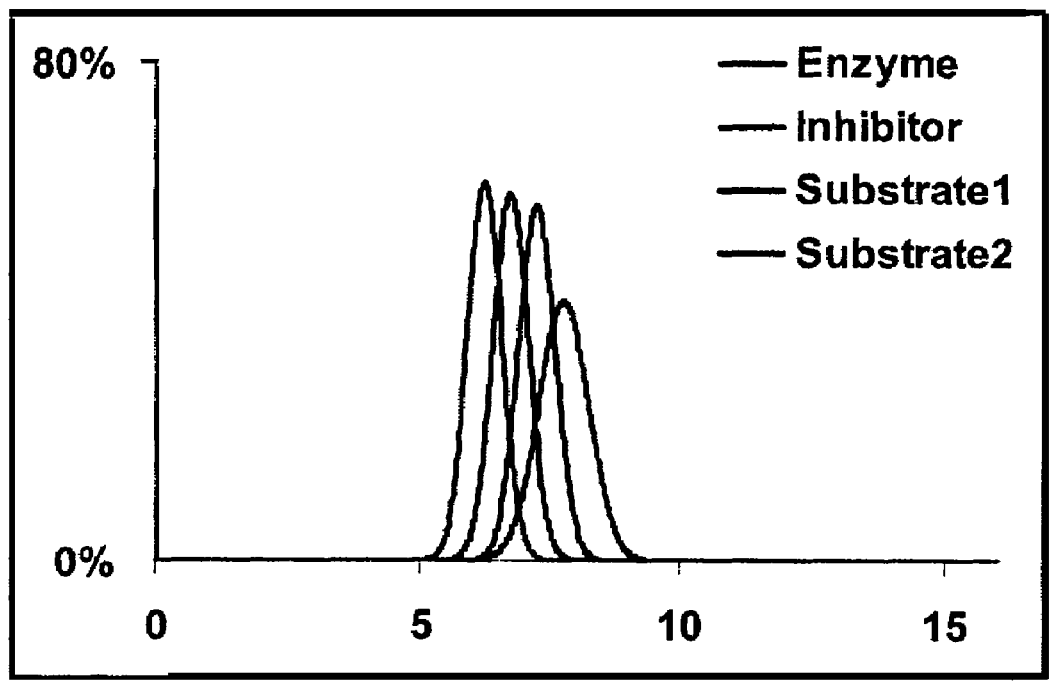
FIG. 9 presents the results of numerical modeling for slow injections, showing final total distributions with respect to capillary length. enzyme=red; inhibitor=black; substrate 1=blue; substrate 2=green

Under the fast-injection conditions, the York number corresponding to both substrate and inhibitor was 1.44, and the York number corresponding to the enzyme was 0.144. For slow injections, the York number corresponding to both substrate and inhibitor was 14.4, and the York number corresponding to the enzyme was 1.44. The results of the numerical modeling for the fast injections are presented in FIG. 8. The level of mixing of substrate 1 and substrate 2 was 57%. The results of the numerical modeling for the slow injections are presented in FIG. 9. The level of substrate mixing for the slow injections (45%) was lower than the level of mixing for the fast injections. For slow injections, the rate of the reaction with zero concentration of inhibitor was approximately 26% of the rate for fast injections. Additionally, according to computer modeling, inhibition for non-zero concentration of inhibitor was more substantial for slow injections than for fast injections. For fast injections, there was a region in the capillary where substrates and enzyme mixed, but the inhibitor was almost not present.

Example 15

Strategies for Increasing Efficiency of Mixing

As previously discussed, efficient mixing of substances can be achieved with low Yo values. Therefore, one strategy for improving mixing is to decrease Yo. The value of Yo can be decreased by decreasing the injection time; decreasing the injection time requires a proportional increase in the pressure. Hydrodynamic inertia along with technical difficulties will limit the level to which the pressure can be increased and the injection time decreased. Realistically, the pressure of several units of atmospheres is achievable, and would allow one to decrease injection times to ~10 ms. In such a case, Yo will be a small value, even for small molecules.

Another strategy for improving mixing involves the use of prolonged mixing injection of a buffer. Essentially, this strategy utilizes Taylor's efficient diffusion in Poiseuille flow in a capillary. Mixing by the last buffer plug improves with a decrease in the usual diffusion. With larger York numbers, the concentration of substances at some distance from the inlet of the capillary is practically null. Therefore, it is possible to vary the mixing injection by changing the sign of pressure, and, accordingly, the direction of Poiseuille flow. Varying the pressure allows unlimited "increase" in the effective time of the mixing injection without a danger of substances exiting the capillary. It is also possible to use multiple injections for every substance, in a "sandwich" approach. Thus, in all cases of practical importance, even where the York number is not small, it is possible to achieve efficient mixing of components. As a rule, efficient mixing can result in the significant dilution of initial substances, particularly in the mixing buffer. Such dilution may be calculated beforehand, and taken into account in the planning of experiments.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for mixing three or more fluids under conditions of laminar flow inside a capillary tube comprising a single inlet comprising the steps of:
   a) analyzing laminar flow profiles of the three or more fluids inside the capillary tube using a mathematical model that analyzes the shapes of the profiles to calculate concentration profiles of mixed fluids, wherein the mathematical model comprises parameters comprising of a coefficient of diffusion of a molecule inside the capillary tube, a diameter of the capillary tube, a time of introduction of a fluid into the capillary tube, a time of incubation of a fluid inside the capillary tube, the number of fluids to be mixed inside the capillary tube, position of at least one fluid on an array of fluids to be mixed inside the capillary tube, molecular weight of at least one solute in at least one fluid to be mixed inside the capillary tube, viscosity of at least one fluid inside the capillary tube, viscosity of at least one fluid to be mixed inside the capillary tube, and volume of at least one fluid to be mixed inside the capillary tube, wherein the model assumes that longitudinal diffusion is negligible;
   b) adjusting one or more of the parameters in the mathematical model to optimize mixing of the calculated concentration profiles, wherein mixing is optimized by adjusting the parameters such that 1) transverse diffusion during injection of fluid plugs is minimized; 2) each pressure injected non-diffused fluid plug has a parabolic profile; 3) after injection of the three or more fluids multiple fluid layers are formed in the transverse direction 4) mixing by transverse diffusion eliminates concentration gradients in the transverse direction;
   c) sequentially injecting the three or more fluids plugs into the single inlet of the capillary tube by pressure injection, under conditions comprising the adjusted parameters from b); and
   d) allowing the three or more fluids to mix inside the capillary tube by transverse diffusion of the parabolic concentration profiles.

2. The method of claim 1, wherein each of the fluids is a liquid.

3. The method of claim 2, wherein each of the fluids is a solution.

4. The method of claim 2, wherein at least one fluid is a solvent, and wherein at least one solute is mixed with the solvent.

5. The method of claim 2, wherein each of the fluids comprises a substance selected from the group consisting of an antibody, an antigen, an aptamer, a buffer, DNA, an enzyme, an enzyme inhibitor, an enzyme substrate, a ligand, a ligand receptor, a protein, and RNA.

6. The method of claim 1, wherein each of the fluids is injected into the capillary tube with an introduction time of 1 second or less.

7. The method of claim 1, wherein the capillary tube is a channel in a microfabricated device.

8. The method of claim 1, wherein the fluids comprise at least two reagents, and wherein a reaction occurs inside the capillary tube upon mixing.

9. The method of claim 8, further comprising the step of separating reaction components, wherein the reaction components are selected from the group consisting of unused reagent and reaction product.

10. The method of claim 9, wherein the reaction components are separated by capillary electrophoresis or capillary chromatography.

11. The method of claim 9, wherein the step of separating reaction components comprises detecting the reaction components during or following separation.

12. The method of claim 11, wherein the reaction components are detected inside the capillary tube, or upon exiting the capillary tube, by absorbance, chemiluminescence, fluorescence, mass spectrometry, or an electrochemical detector.

13. The method of claim 8, wherein the at least two reagents comprise at least one enzyme and at least one enzyme.

14. The method of claim 13, further comprising the step of screening for at least one enzyme-substrate complex.

15. The method of claim 13, further comprising the step of screening for at least one enzyme inhibitor.

16. The method of claim 15, wherein the step of screening for at least one enzyme inhibitor comprises measuring inhibition efficiency of the at least one enzyme inhibitor.

17. The method of claim 8, wherein the at least two reagents comprise at least one antigen and at least one antibody, at least one aptamer and at least one target thereof, at least one DNA-binding protein and at least one DNA, at least one RNA-binding protein and at least one RNA, or at least one ligand and at least one receptor.

18. The method of claim 17, further comprising the step of detecting or measuring binding between the at least two reagents.

19. The method of claim 8, wherein the at least two reagents comprise at least one drug candidate and at least one therapeutic target.

20. The method of claim 19, wherein the therapeutic target is a protein.

21. The method of claim 19, further comprising the step of detecting or measuring binding of the drug candidate and the therapeutic target.

22. The method of claim 21, wherein the step of detecting or measuring binding comprises high-throughput screening.

23. The method of claim 19, further comprising the step of screening for at least one drug-target complex.

24. The method of claim 1, wherein the parabolic concentration profile for each fluid is eliminated by the transverse diffusion.

25. The method of claim 1 comprising mixing of four fluids wherein the first three fluids are solutions comprising a solute and a solvent and the fourth fluid is a solvent with no solute.

26. The method of claim 1, wherein steps (a) and (b) are implemented by a computer comprising at least one processor.

* * * * *